US00PP17256P2

(12) United States Plant Patent
Pierce

(10) Patent No.: US PP17,256 P2
(45) Date of Patent: Dec. 5, 2006

(54) ***CALIBRACHOA* PLANT NAMED 'CAL CREMEY'**

(50) Latin Name: ***Calibrachoa* sp.**
Varietal Denomination: Cal Cremey

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 43 days.

(21) Appl. No.: 11/352,598

(22) Filed: Feb. 13, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—Jondle & Associates P.C.

(57) ABSTRACT

A new *Calibrachoa* plant particularly distinguished by medium, cream-white flowers with red markings and yellow throats, early and continuous flowering, medium green foliage with lanceolate leaves, a medium size, medium vigor, bushy, and a spreading to semi-trailing plant habit with good branching ability, is disclosed.

2 Drawing Sheets

Genus and species: *Calibrachoa* sp.
Variety denomination: 'Cal Cremey'.

BACKGROUND OF THE NEW PLANT

The present invention comprises a new and distinct cultivar of *Calibrachoa,* botanically known as *Calibrachoa* sp., and hereinafter referred to by the cultivar name 'Cal Cremey'. The new cultivar originated from a hybridization made in October 2001 in Gilroy, Calif. The female parent was the proprietary pale-rose flowered *Calibrachoa* plant '389-1' (unpatented), while the male parent was the proprietary *Calibrachoa* plant '355-1' (unpatented) having pale-orange flowers with an eye. The seeds produced by the hybridization were sown in April 2002 in Gilroy, Calif. A single plant selection was chosen for further evaluation and for asexual propagation in Summer 2002 in Gilroy, Calif.

The new cultivar was created in 2002 in Gilroy, Calif. and has been asexually reproduced repeatedly by vegetative cuttings and tissue culture in Gilroy, Calif. over a two-year period. 'Cal Cremey' has not been observed under all possible environmental conditions. The present invention has been found to retain its distinctive characteristics through successive asexual propagations.

Plant Breeder's Rights for this cultivar were applied for in Canada on Jul. 19, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Medium, cream-white flowers with red markings and yellow throats;
2. Medium-green foliage with lanceolate leaves;
3. Medium size, bushy, plant habit;
4. A spreading to semi-trailing plant habit;
5. Good branching ability with medium vigor; and
6. An early and continuous flowering response.

DESCRIPTION OF PHOTOGRAPHS

This new *Calibrachoa* plant is illustrated by the accompanying photographs which show overall plant habit including blooms, buds, and foliage of the plant; the colors shown are as true as can be reasonably obtained by conventional photographic procedures. The photographs are of plants grown in a greenhouse in Hillscheid, Germany.

DESCRIPTION OF THE NEW CULTIVAR

Figure 1:
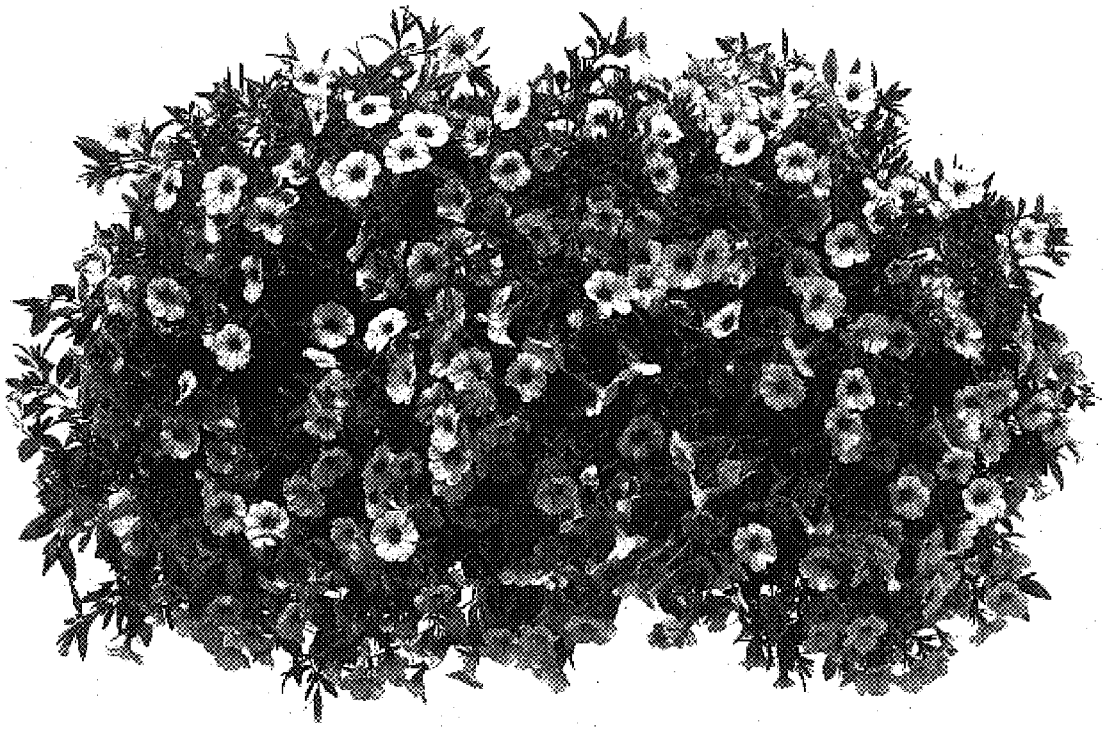
FIG. 1 shows the overall plant habit, including blooms, buds and foliage of a 25-week old plant in late Summer of 2005.
Figure 2:
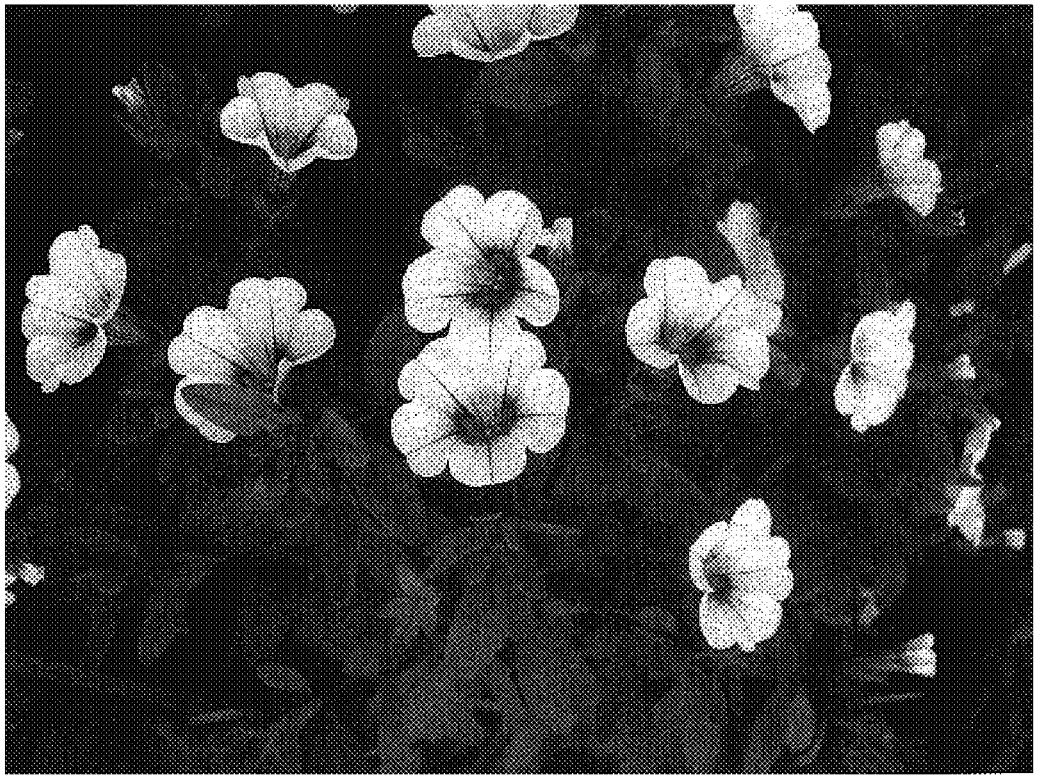
FIG. 2 shows a close-up of the mature inflorescences of an 11-week old plant in May 2005.

The following detailed description sets forth the distinctive characteristics of 'Cal Cremey'. The data which define these characteristics were collected from asexual reproductions carried out in Hillscheid, Germany. The plant history was taken on 6-week old unpinched plants which were planted as rooted cuttings in 12-cm pots in July 2005, and then grown in a greenhouse. Observations were made when the plants were in full flower in August 2005. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
*Family.*—Solanaceae.
*Botanical.*—*Calibrachoa* sp.
*Common name.*—*Calibrachoa.*

Parentage:
*Female parent.*—'389-1' a proprietary pale-rose flowered *Calibrachoa* plant (unpatented).
*Male parent.*—'355-1', a proprietary *Calibrachoa* plant having pale-orange flowers with an eye (unpatented).

Growth:

*Form.*—Herbaceous perennial, usually cultivated as an annual plant.

*Habit.*—Spreading initially, decumbent or semi-trailing plant habit later; free branching; relatively compact and tight habit.

*Height* (*measured from the top of the soil*).—9.1 cm for a 9-week old plant.

*Width* (*horizontal plant diameter*).—33.9 cm.

*Propagation.*—Terminal tips for cuttings.

*Time to produce a finished flowering plant.*—9 to 10 weeks for a 12-cm pot.

*Outdoor plant performance.*—For hanging baskets and container planting.

*Time to initiate and develop roots.*—About 24 days.

*Root description.*—Fibrous, self-branching.

Stems:

*Average number* (*basal plus secondary*).—17.1.

*Length of basal branches* (*from the base of the stem to the tip*).—20 cm.

*Internode length.*—1.0 cm to 2.0 cm.

*Diameter of branches* (*from midpoint*).—0.2 cm to 0.3 cm.

*Stem color.*—RHS 143C (green), partly infused with anthocyanin RHS 166A (brown) or lighter.

*Texture.*—Somewhat rough with very short hair.

Leaves:

*Arrangement.*—Initially alternate, later appear mostly opposite with flowering branches.

*Size.*—Length: 4.5 cm. Width: 1.2 cm.

*Shape.*—Lanceolate to narrowly elliptic.

*Margin.*—Entire.

*Apex.*—Acute to obtuse.

*Base.*—Attenuate.

*Color* (*mature leaves*).—Upper surface: RHS 137C (medium green) to RHS 138A. Lower surface: RHS 143C.

*Texture.*—Velvety, very short pubescence.

*Venation.*—Pinnate, mostly indistinct.

*Venation color.*—RHS 145C for the midrib of the lower surface.

*Variegation.*—None.

*Petioles.*—Length: 0.3 cm to 0.5 cm (not clearly distinct from the base of the leaf). Width: 0.1 cm to 0.2 cm. Color: RHS 145B (pale light-green) to RHS 145C, both sides. Texture: Covered with pubescence.

Flower bud:

*Shape.*—Tube-shaped with the corolla end somewhat furrowed and folded lengthwise.

*Size.*—Length: 2.0 cm. Diameter: 0.4 cm to 0.5 cm.

*Color at tight bud.*—RHS 12C (yellowish), RHS 11D for the lobes.

Inflorescence:

*Blooming habit.*—Continuous from Spring to Fall.

*Inflorescence type.*—Flowers appear solitary, emerging from the leaf axil.

*Floret type.*—Base is funnel-shaped with fused petals; upper part is salver-shaped and slightly zygomorphic.

*Number of flowers per node.*—One.

*Lastingness of individual blooms on the plant.*—6 days.

*Size.*—Diameter (flower face): 2.9 cm. Length (flower face): 2.7 cm. Depth (total length of flower): 2.3 cm. Funnel: Length (from below): 1.7 cm. Diameter (at opening): 0.9 cm.

*Fragrance.*—Weak, petunia-like.

*Peduncle.*—Color: RHS 143C. Length: 3.0 cm to 4.0 cm. Diameter: 0.1 cm. Texture: Covered with dense pubescence.

Flowers:

*Immature flower.*—Diameter: 2.6 cm. Color: RHS 2D.

*Mature flower color.*—RHS 4D at the petal lobes.

*Corolla.*—Shape of corolla: Tube-shaped. Color inside: RHS 7B (yellow), weakly lined; RHS 46D (reddish) ring surrounding three sides of the opening and RHS 9A (deep yellow) lower lip at the fourth side. Color outside: RHS 160B (yellowish), with fine, dark veins. Outside texture: Somewhat rippled and covered with glandular hair.

*Petals.*—Shape: Lower part is fused and upper part is a free lobe. Apex: Mostly truncate, may be weakly emarginate. Base: Fused. Margin: Entire. Waviness of petals: Absent. Lobation: Relatively weak. Texture: Smooth, slightly glossy.

*Sepals.*—Shape: Lanceolate. Apex: Acute. Base: Fused. Margin: Entire. Length: 1.4 cm. Width: 0.3 cm. Color: RHS 143B (green). Texture: Fine pubescence. Pubescence color: Whitish.

Reproductive organs:

*Stamens.*—Number: 5 (various lengths). Filament color: RHS 155A (whitish). Filament length: 0.7 cm to 1.1 cm. Filament diameter: 0.1 cm. Pollen color: RHS 6D (light-yellow). Pollen quantity: Moderate.

*Pistils.*—Number: 1. Length: 1.0 cm. Diameter: 0.1 cm. Stigma color: RHS 143C (green). Style color: RHS 143D (light-green).

Fruit and seed set: No seed set observed.

Disease and insect resistance: No particular resistance or susceptibility has been observed.

COMPARISON WITH PARENTAL AND COMMERCIAL CULTIVARS

'Cal Cremey' differs from the female parent '389-1' (unpatented), by having large, cream-white flowers, while '389-1' has smaller, pale-rose flowers. In addition, 'Cal Cremey' has a more upright, less decumbent plant habit than '389-1'.

'Cal Cremey' differs from the male parent '355-1' (unpatented), by having cream-white flowers, while '355-1' has pale-orange flowers. In addition, 'Cal Cremey' has smaller leaves and more basal branching than '355-1'.

'Cal Cremey' differs from the commercial cultivar 'Cal Ivory' (U.S. Plant Pat. No. 14,544), by having cream-white flowers with a more distinct yellow throat and a red ring, while 'Cal Ivory' has light yellow flowers with a less distinct yellow throat and no red ring. In addition, 'Cal Cremey' has shorter branches (about 70% of the length) than 'Cal Ivory'.

I claim:

1. A new and distinct cultivar of *Calibrachoa* plant as shown and described herein.

* * * * *